(12) United States Patent
Johnson et al.

(10) Patent No.: US 10,699,802 B2
(45) Date of Patent: Jun. 30, 2020

(54) MICROSATELLITE INSTABILITY CHARACTERIZATION

(71) Applicant: Strata Oncology, Inc., Ann Arbor, MI (US)

(72) Inventors: Bryan Johnson, Ann Arbor, MI (US); Dan Rhodes, Ann Arbor, MI (US); Scott Tomlins, Ann Arbor, MI (US)

(73) Assignee: Strata Oncology, Inc., Ann Arbor, MI (US)

( * ) Notice: Subject to any disclaimer, the term of this patent is extended or adjusted under 35 U.S.C. 154(b) by 0 days.

(21) Appl. No.: 16/155,667

(22) Filed: Oct. 9, 2018

(65) Prior Publication Data

US 2019/0108312 A1    Apr. 11, 2019

Related U.S. Application Data

(60) Provisional application No. 62/569,821, filed on Oct. 9, 2017.

(51) Int. Cl.
| | | |
|---|---|---|
| *G01N 33/48* | (2006.01) | |
| *G16B 40/00* | (2019.01) | |
| *G16B 20/00* | (2019.01) | |
| *G16B 30/00* | (2019.01) | |

(52) U.S. Cl.
CPC ............ *G16B 40/00* (2019.02); *G16B 20/00* (2019.02); *G16B 30/00* (2019.02)

(58) Field of Classification Search
None
See application file for complete search history.

(56) References Cited

U.S. PATENT DOCUMENTS

| | | |
|---|---|---|
| 6,150,100 A | 11/2000 | Rueschoff et al. |
| 6,844,152 B1 | 1/2005 | Bacher et al. |
| 2004/0175700 A1 | 9/2004 | Geesaman |
| 2005/0202473 A1 | 9/2005 | Bacher et al. |
| 2006/0068385 A1 | 3/2006 | Hamelin et al. |
| 2012/0295267 A1 | 11/2012 | Goel et al. |
| 2015/0031551 A1* | 1/2015 | Sikora ............ G06F 19/22 506/2 |
| 2015/0045369 A1 | 2/2015 | Lambrechts |
| 2015/0051116 A1 | 2/2015 | Kim |
| 2015/0094211 A1* | 4/2015 | Vander Horn ....... C12N 9/1252 506/2 |
| 2016/0040254 A1 | 2/2016 | Garner et al. |
| 2017/0213008 A1 | 7/2017 | Venn |
| 2018/0203974 A1 | 7/2018 | Venn |
| 2019/0194731 A1* | 6/2019 | Burn ............ C12Q 1/6827 |

FOREIGN PATENT DOCUMENTS

| | | |
|---|---|---|
| WO | 2016127067 A1 | 8/2016 |
| WO | 2017112738 A1 | 6/2017 |
| WO | 2017114851 A1 | 7/2017 |
| WO | 2018037231 A1 | 3/2018 |

OTHER PUBLICATIONS

Buecher et al. "Role of microsatellite instability in the management of colorectal cancers" (Digestive and Liver Diseases, vol. 45 (2013) pp. 441-449).*
Choi, Sang-Wook, et al. "Genetic classification of colorectal cancer based on chromosomal loss and microsatellite instability predicts survival." Clinical cancer research 8.7 (2002): 2311-2322.*
Hause, Ronald J., et al., "Classification and characterization of microsatellite instability across 18 cancer types", Nature Medicine, vol. 22, pp. 1342-1352, Nov. 11, 2016, 1342-1352.
Quail, Michael A., et al., "A tale of three next generation sequencing platforms: comparison of Ion Torrent, Pacific Biosciences and Illumina MiSeq sequencers", BMC Genomics, vol. 13, 2012.
Salipante, Stephen J., et al., "Microsatellite Instability Detection by Next Generation Sequencing", Clinical Chemistry, vol. 60, pp. 1192-1199, Sep. 1, 2014, 1192-1199.
"International Search Report and Written Opinion of the ISA, dated Jan. 8, 2019, for application No. PCT/US19/055071."
Kumar, Vipin, et al., "Comparative Analysis of Diversity Based on Morpho-Agronomic Traits and Microsatellite Markers in Common Bean,", Euphytica, May 28, 2009, vol. 170, pp. 249-262.
Rabbee, Nusrat, et al., "A genotype Calling Algorithm for Affymetrix SNP Arrays,", Bioinformatics, Nov. 2, 2005, vol. 22, Iss. 1, pp. 7-12.
Rousett, Francois, et al., "GENEPOP'007: a Complete Re-Implementation of the GENPOP Software for Windows and Linux,", Molecular Ecology Resources, Jun. 28, 2008, vol. 8, No. 1, pp. 103-106.
Taback, Bret, et al., "Prognostic Significance of Circulating Microsatellite Markers in the Plasma of Melanoma Patients,", Cancer Research, Aug. 1, 2001, vol. 61, pp. 5723-5726.

* cited by examiner

*Primary Examiner* — Anna Skibinsky
(74) *Attorney, Agent, or Firm* — Morse, Barnes-Brown & Pendleton, P.C.; Lisa M. Warren, Esq.

(57) ABSTRACT

Embodiments of a method and/or system (e.g., for microsatellite instability detection associated with at least one cancer condition; etc.) can include: determining a microsatellite-related background model; determining one or more loci associated with microsatellite instability based on the microsatellite-related background model; and/or determining a microsatellite instability characterization (e.g., a binary status determination between microsatellite instability such as MSI-H, and microsatellite stability such as MSS; etc.) for the user. Additionally or alternatively, embodiments of the method and/or system can include facilitating treatment provision for one or more users based on the microsatellite instability characterization.

18 Claims, 5 Drawing Sheets

```
┌─────────────────────────────────────────────────────────────────┐
│  determining a microsatellite stability background model based  │
│  on a set of observed variant allele frequencies from a first   │
│  set of samples associated with microsatellite stability S110   │
│  ┌───────────────────────────────────────────────────────────┐  │
│  │      performing a scale normalization based on the        │  │
│  │            observed variant allele frequencies            │  │
│  └───────────────────────────────────────────────────────────┘  │
└─────────────────────────────────────────────────────────────────┘
                                  │
                                  ▼
┌─────────────────────────────────────────────────────────────────┐
│  determining a set of loci associated with microsatellite       │
│  instability based on the microsatellite stability background   │
│  model and a second set of samples associated with the          │
│  microsatellite instability S120                                │
└─────────────────────────────────────────────────────────────────┘
                                  │
                                  ▼
┌─────────────────────────────────────────────────────────────────┐
│       determining a microsatellite instability characterization S130 │
│  ┌───────────────────────────────────────────────────────────┐  │
│  │  determining a microsatellite instability threshold based │  │
│  │  on the set of loci and a third set of samples associated │  │
│  │  with the microsatellite stability and the microsatellite │  │
│  │  instability                                              │  │
│  └───────────────────────────────────────────────────────────┘  │
│  ┌───────────────────────────────────────────────────────────┐  │
│  │  determining a microsatellite instability parameter for a │  │
│  │  user associated with a user sample, based on the user    │  │
│  │  sample and the set of loci                               │  │
│  └───────────────────────────────────────────────────────────┘  │
│  ┌───────────────────────────────────────────────────────────┐  │
│  │  determining a microsatellite instability characterization│  │
│  │  for the user based on a comparison between the           │  │
│  │  microsatellite instability parameter and the             │  │
│  │  microsatellite instability threshold                     │  │
│  └───────────────────────────────────────────────────────────┘  │
└─────────────────────────────────────────────────────────────────┘
                                  │
                                  ▼
┌─────────────────────────────────────────────────────────────────┐
│  facilitating treatment provision for the user for one or more  │
│            microsatellite-associated conditions S140            │
└─────────────────────────────────────────────────────────────────┘
```

FIGURE 2 determining a microsatellite instability characterization (e.g., based on a microsatellite instability parameter such as an overall log-likelihood ratio of distances) S130 determining a microsatellite instability parameter for a user associated with a user sample, based on the user sample and a set of loci associated with microsatellite instability determining a microsatellite stability distance for the user based on the user sample and a microsatellite stability background model (e.g., an MSS background model) associated with first variant allele frequencies from first samples associated with microsatellite stability determining a microsatellite instability distance for the user based on the user sample and a microsatellite instability background model (e.g., an MSI background model, such as an MSI-H background model; etc.) associated with second variant allele frequencies from second samples associated with the microsatellite instability facilitating treatment provision for the user for one or more microsatellite-associated conditions S140

MICROSATELLITE INSTABILITY CHARACTERIZATION

CROSS-REFERENCE TO RELATED APPLICATIONS

This application claims the benefit of U.S. Provisional Application No. 62/569,821 filed 9 Oct. 2017, which is herein incorporated in its entirety by this reference.

TECHNICAL FIELD

This disclosure generally relates to microsatellite instability and genomics.

BACKGROUND

Microsatellite instability (MSI) can be characterized by increased mutational load in repetitive DNA tracts (e.g., resulting from impaired DNA mismatch repair, leading to increased predisposition to mutation, etc.), such as repeated sequences of DNA (e.g., repeating units of 1-6 bp each). MSI has been shown as an indicator of treatment response, as a diagnostic phenotype in colorectal, endometrial and gastrointestinal cancers, and is recognized as an important pan-cancer biomarker. For example, MSI-high (MSI-H) has been shown as an indicator for pembrolizumab in advanced solid tumors.

DESCRIPTION OF THE EMBODIMENTS

The following description of the embodiments is not intended to limit the embodiments, but rather to enable any person skilled in the art to make and use.
1. Overview.

Figure 1:
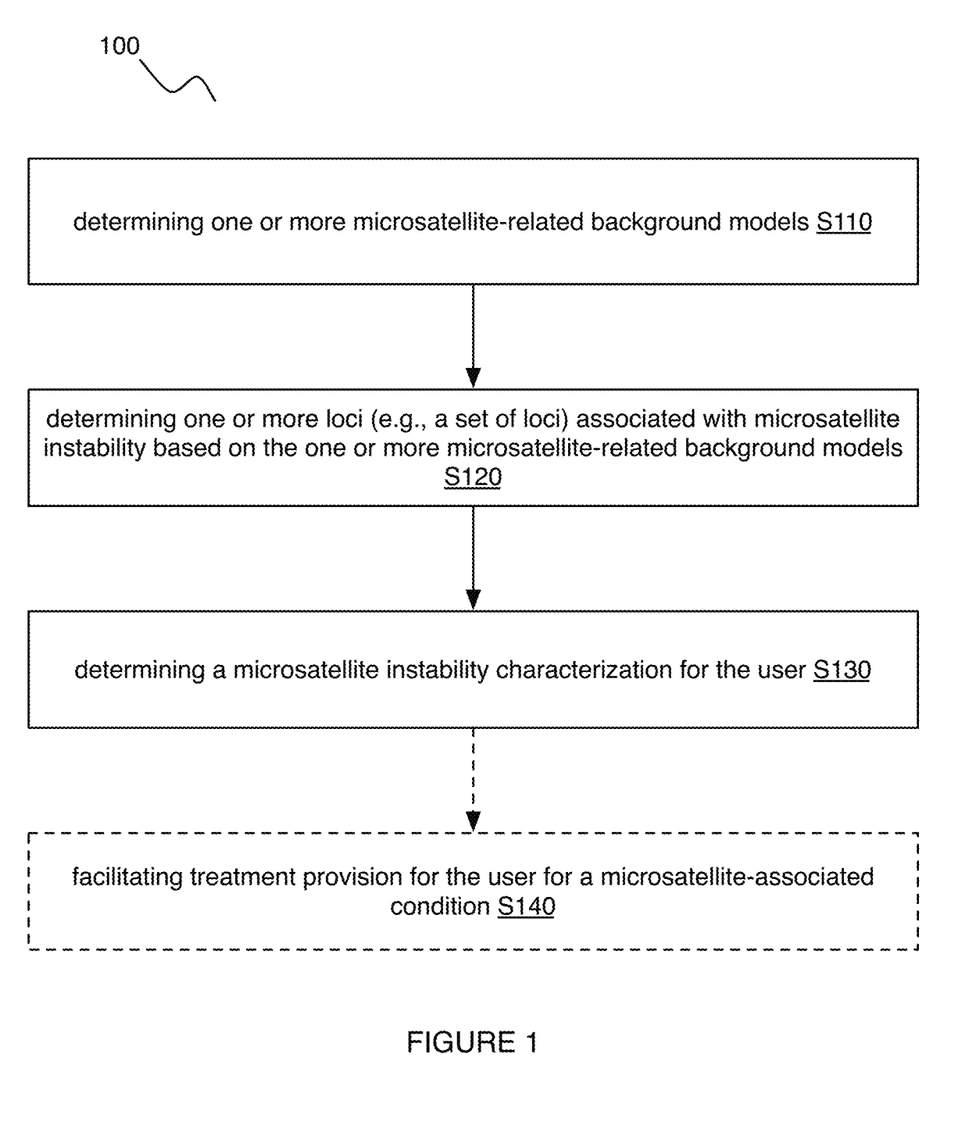
FIG. 1 includes a flow representation of variations of an embodiment of a method.
Figure 2:
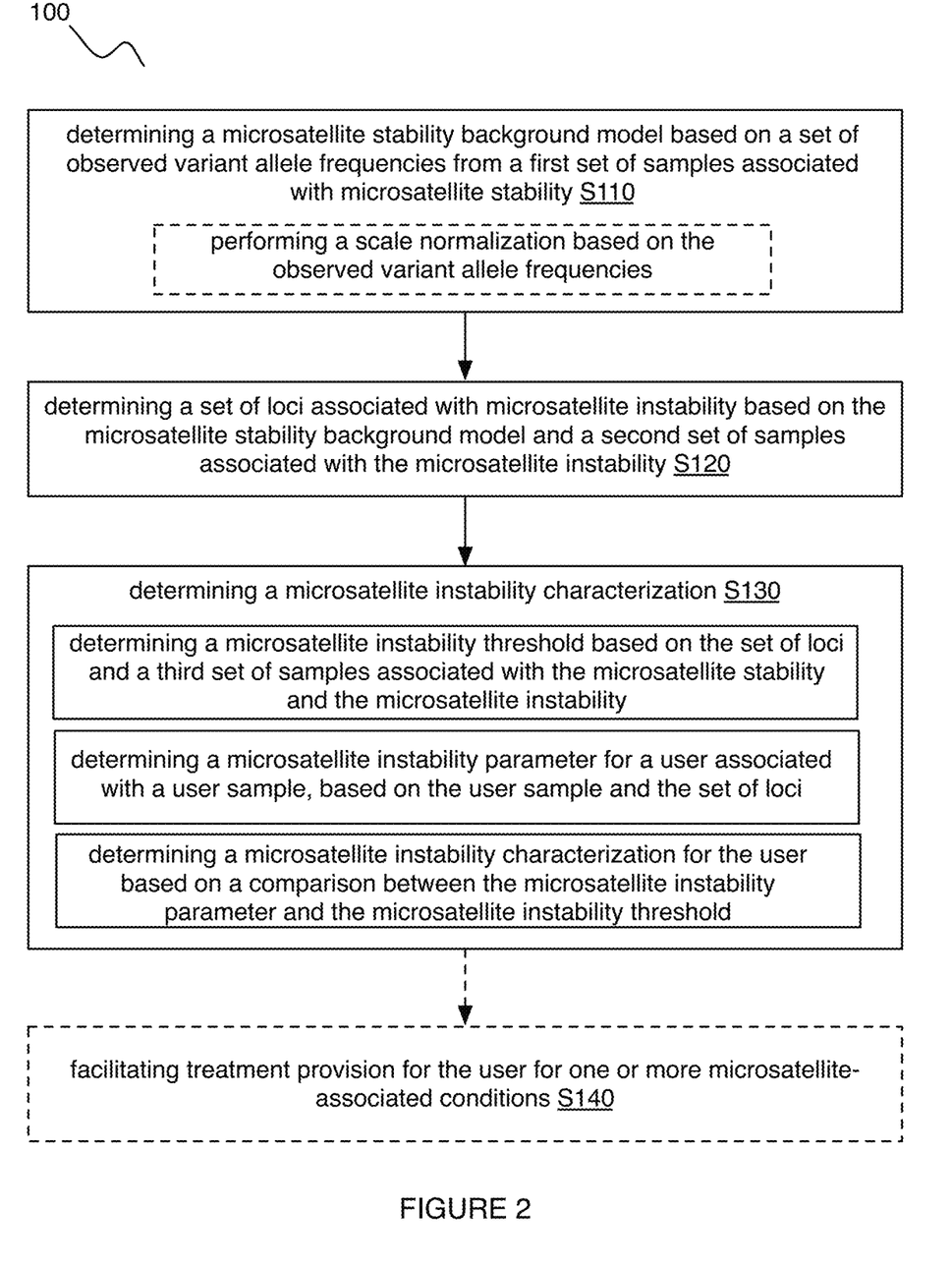
FIG. 2 includes a flow representation of variations of an embodiment of a method.
Figure 4:
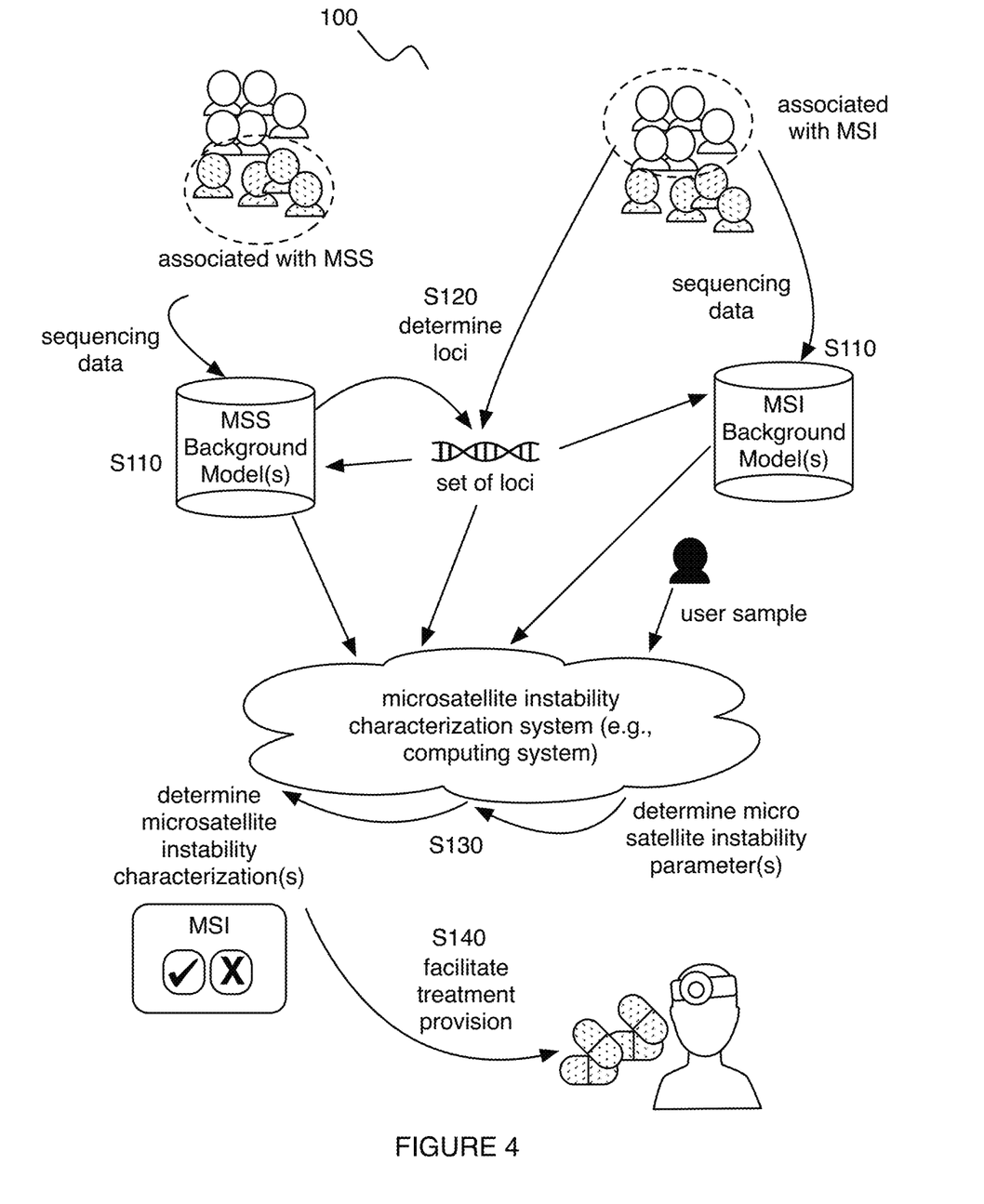
FIG. 4 includes a schematic representation of variations of an embodiment of a method.

As shown in FIGS. 1-2 and 4, embodiments of a method 100 (e.g., for microsatellite instability detection associated with at least one cancer condition; etc.) can include: determining one or more microsatellite-related background models Silo (e.g., a microsatellite stability background model; a microsatellite instability background model; etc.); determining one or more loci (e.g., a set of loci) associated with microsatellite instability based on the one or more microsatellite-related background models S120; and/or determining a microsatellite instability characterization (e.g., a binary status determination between microsatellite instability such as MSI-H, and microsatellite stability (MSS); a microsatellite instability characterization associated with at least one cancer condition; etc.) for the user (e.g., based on a comparison between a microsatellite instability parameter and a microsatellite instability threshold; etc.) S130. Additionally or alternatively, embodiments of the method 100 can include facilitating treatment provision for one or more users based on the microsatellite instability characterization; and/or can include any suitable processes.

In a specific example, as shown in FIG. 2, a method 100 (e.g., for microsatellite instability detection associated with at least one cancer condition; etc.) can include: determining a microsatellite stability background model (e.g., an MSS background model) based on a set of observed variant allele frequencies from a first set of samples associated with microsatellite stability, where determining the microsatellite stability background model includes performing a scale normalization based on the observed variant allele frequencies (e.g., normalizing observed variant allele frequencies of the set of observed variant allele frequencies based on a single-base deletion variant allele frequency; etc.); determining a set of loci associated with microsatellite instability based on the microsatellite stability background model and a second set of samples associated with the microsatellite instability; determining a microsatellite instability threshold based on the set of loci and a third set of samples associated with the microsatellite stability and the microsatellite instability; determining a microsatellite instability parameter for a user associated with a user sample, based on the user sample and the set of loci; and/or determining a microsatellite instability characterization (e.g., detection of microsatellite stability or instability; associated with the at least one cancer condition, etc.) for the user based on a comparison between the microsatellite instability parameter and the microsatellite instability threshold.

Figure 3:
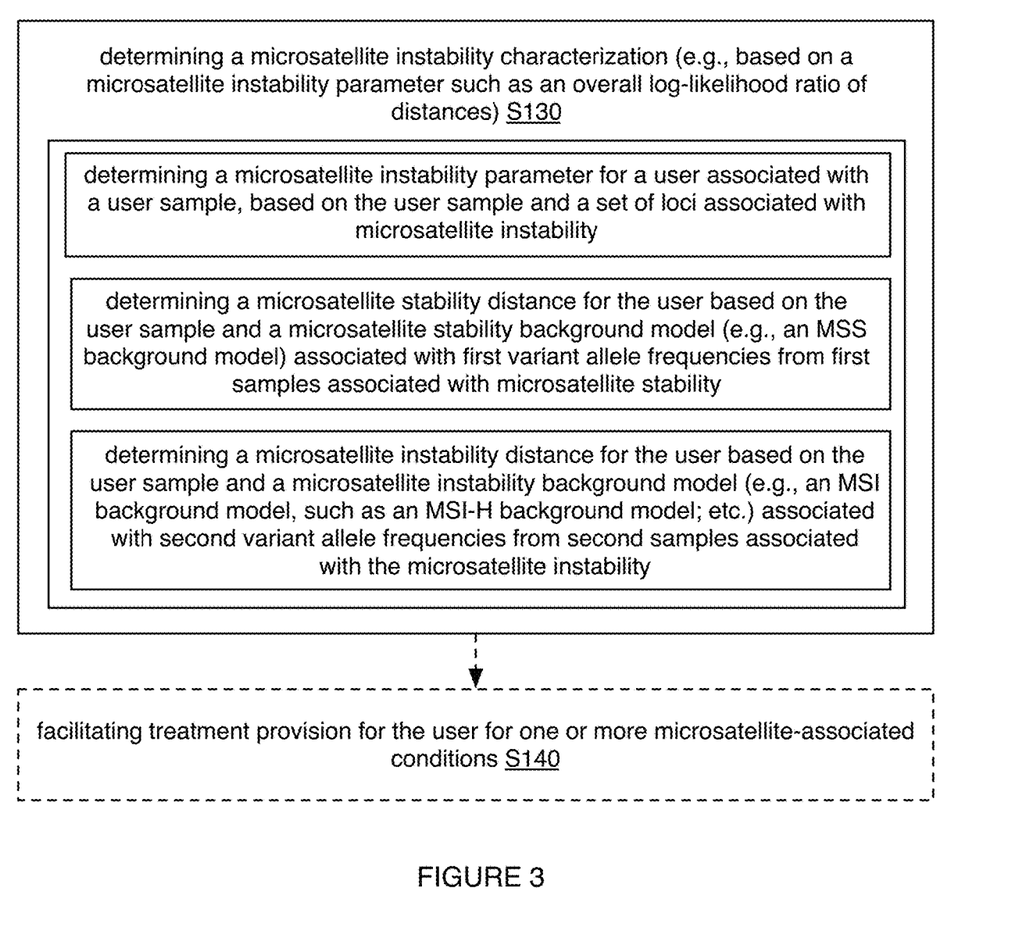
FIG. 3 includes a flow representation of variations of determining a microsatellite instability characterization.

In a specific example, as shown in FIG. 3, a method 100 (e.g., for microsatellite instability detection; etc.) can include: determining a microsatellite instability parameter for a user associated with a user sample, based on the user sample and a set of loci associated with microsatellite instability, where determining the microsatellite instability parameter includes: determining a microsatellite stability distance for the user based on the user sample and a microsatellite stability background model (e.g., an MSS background model) associated with first variant allele frequencies from first samples associated with microsatellite stability, and determining a microsatellite instability distance for the user based on the user sample and a microsatellite instability background model (e.g., an MSI background model, such as an MSI-H background model; etc.) associated with second variant allele frequencies from second samples associated with the microsatellite instability; and determining a microsatellite instability characterization (e.g., detection of microsatellite stability or instability; etc.) for the user based on the microsatellite instability parameter.

Embodiments of the method 100 and/or system 200 can function to determine one or more microsatellite instability characterizations (e.g., determining presence, degree of, detection of, microsatellite instability; etc.) for one or more users. In a specific example, the method 100 can include determining a set of loci associated with microsatellite instability (e.g., identifying microsatellites most enriched for increased mutational load in samples associated with microsatellite instability; etc.) and determining microsatellite instability characterizations for one or more users (e.g., characterizing the set of loci as either stable or unstable in novel user samples, based on the number of observed variant alleles, such as in relation to background models for microsatellite stability and/or microsatellite instability; etc.). In examples, embodiments of the method 100 and/or system 200 can determine microsatellite instability characterizations for evaluating user response to one or more treatments (e.g., pembrolizumab, immunotherapy treatments, etc.) for one or more microsatellite instability-associated conditions (e.g., cancer conditions, such as advanced solid tumors, such as for colorectal, endometrial, and/or gastrointestinal tumors; etc.). In examples, embodiments of the method 100 and/or system 200 can determine microsatellite instability characterizations to facilitate diagnosis (e.g., leveraging microsatellite instability as a biomarker, etc.) of one or more microsatellite instability-associated conditions (e.g., colorectal, endometrial, and/or gastrointestinal cancer; Lynch syndrome; etc.). In examples, embodiments of the method 100 and/or system 200 can additionally or alternatively function to overcome (e.g., account for, accommodate, balance out, etc.) sequencing-associated (e.g., associated with sequencing library preparation; associated with sequencing systems; etc.) errors. In specific examples, embodiments of the method 100 and/or system 200 can function to overcome homopolymer-associated errors (e.g., inaccuracies in sequencing homopolymer regions of genetic sequences, such as in relation to accurately determining the correct number of nucleotide repeats in nucleotide repeat regions associated with microsatellites; such as where short homopolymer regions can be overrepresented; such as where long homopolymer regions can be underrepresented; such as where an accuracy dependence on homopolymer length can be present; such as errors associated with variable homopolymer error-based indel scale; such as errors associated with sequencing mononucleotide repeats and/or suitable types predictive and/or otherwise associated microsatellite instability; etc.) associated with sequencing systems 220 (e.g., semiconductor-based sequencing systems such as Thermo Fisher Scientific Ion Torrent sequencing systems; next-generation sequencing systems; etc.).

In a specific example, embodiments of the method 100 and/or system 200 can determine a binary status of microsatellite instability (e.g., MSI-H) or microsatellite stability (e.g., MSS), such as with high sensitivity (e.g., greater than 85%), high specificity (e.g. greater than 99%), and high reproducibility (e.g., greater than 99%). However, embodiments of the method 100 and/or system 200 can be associated with any suitable accuracy, sensitivity, specificity, reproducibility, and/or other suitable metrics in relation to determining one or more microsatellite instability characterizations.

Portions of Embodiments of the method 100 and/or system 200 can additionally or alternatively be associated with (e.g., relate to, correspond to, etc.) one or more microsatellite instability-associated conditions. In examples, the method 100 can include a determining a microsatellite instability characterization associated with one or more microsatellite instability-associated conditions (e.g., informative of one or more microsatellite instability-associated conditions; informative of treatment response for one or more microsatellite instability-associated conditions; diagnostic of one or more microsatellite instability-associated conditions; etc.). In examples, the method 100 can include facilitating treatment provision (e.g., causing treatment provision; providing treatments and/or promoting treatments such as recommending treatments; administering treatments; etc.) for one or more microsatellite instability-associated conditions.

Microsatellite instability-associated conditions can include one or more of: cancer conditions (e.g., colon cancer, gastric cancer, endometrium cancer, ovarian cancer, hepatobiliary tract cancer, urinary tract cancer, stomach cancer, small intestine cancer, brain cancer, skin cancer, any suitable cancer types, etc.); Lynch syndrome; Muir-Torre syndrome; and/or any other suitable conditions associated with microsatellites. Microsatellite instability-associated conditions can include one or more: diseases, symptoms, causes (e.g., triggers, etc.), disorders, associated risk (e.g., propensity scores, etc.), associated severity, associated behaviors, and/or any other suitable aspects associated with microsatellite instability-associated conditions. However, microsatellite instability-associated conditions can be configured in any suitable manner.

Portions of embodiments of the method 100 and/or system 200 preferably apply, include, and/or are otherwise associated with amplicon-based next-generation sequencing (e.g., processing amplicon-based next-generation sequencing data for determining one or more microsatellite instability characterizations, etc.). In a specific example, portions of embodiments of the method 100 and/or systems 200 (e.g., sequencing systems 220, etc.) can include, apply, and/or otherwise be associated with semiconductor-based sequencing technologies (e.g., Thermo Fisher Scientific Ion Torrent Sequencing System). Additionally or alternatively, any suitable portions of embodiments of the method 100 and/or systems 200 (e.g., sequencing systems 220, etc.) can include, apply, and/or otherwise be associated with any suitable sequencing technologies (e.g., sequencing library preparation technologies; sequencing systems 220; sequencing output analysis technologies; systems and/or technologies associated with homopolymer-associated sequencing errors, such as errors in accurately determining the number of DNA repeats, such as where portions of the method 100 and/or systems 200 can function to overcome such errors; etc.). Sequencing technologies preferably include next-generation sequencing technologies. Next-generation sequencing technologies can include any one or more of high-throughput sequencing (e.g., facilitated through high-throughput sequencing technologies; massively parallel signature sequencing, Polony sequencing, 454 pyrosequencing, Illumina sequencing, SOLiD sequencing, Ion Torrent semiconductor sequencing and/or other suitable semiconductor-based sequencing technologies, DNA nanoball sequencing, Heliscope single molecule sequencing, Single molecule real time (SMRT) sequencing, Nanopore DNA sequencing, etc.), any generation number of sequencing technologies (e.g., second-generation sequencing technologies, third-generation sequencing technologies, fourth-generation sequencing technologies, etc.), sequencing-by-synthesis, tunnelling currents sequencing, sequencing by hybridization, mass spectrometry sequencing, microscopy-based techniques, and/or any suitable next-generation sequencing technologies.

Additionally or alternatively, sequencing technologies can include any one or more of: capillary sequencing, Sanger sequencing (e.g., microfluidic Sanger sequencing, etc.), pyrosequencing, nanopore sequencing (Oxford nanopore sequencing, etc.), and/or any other suitable types of sequencing facilitated by any suitable sequencing technologies.

Portions of embodiments of the method 100 and/or portions of embodiments of the system 100 can include, apply, perform, and/or otherwise be associated with any one or more of: sequencing operations, alignment operation (e.g., sequencing read alignment; etc.), lysing operations, cutting operations, tagging operations (e.g., with barcodes; etc.), ligation operations, fragmentation operations, amplification operations (e.g., helicase-dependent amplification (HDA), loop mediated isothermal amplification (LAMP), self-sustained sequence replication (3SR), nucleic acid sequence based amplification (NASBA), strand displacement amplification (SDA), rolling circle amplification (RCA), ligase chain reaction (LCR), etc.), purification operations, cleaning operations, suitable operations for sequencing library preparation, suitable operations for facilitating sequencing and/or downstream analysis, suitable sample processing operations, and/or any suitable sample- and/or sequence-related operations.

Additionally or alternatively, data described herein (e.g., models, parameters, characterizations, treatment determinations, sample data, sequencing data, variant allele frequencies, etc.) can be associated with any suitable temporal indicators (e.g., seconds, minutes, hours, days, weeks, time periods, time points, timestamps, etc.) including one or more: temporal indicators indicating when the data was collected, determined, transmitted, received, and/or otherwise processed; temporal indicators providing context to content described by the data; changes in temporal indicators (e.g., data over time; change in data; data patterns; data trends; data extrapolation and/or other prediction; etc.); and/or any other suitable indicators related to time.

Additionally or alternatively, parameters, metrics, inputs, outputs, and/or other suitable data can be associated with value types including any one or more of: distances (e.g., Mahalanobis distances, etc.), scores (e.g., indicative of presence of, absence of, degree of microsatellite instability; etc.), binary values (e.g., binary status determinations of microsatellite instability or microsatellite stability; etc.), classifications (e.g., multi-label classifications of MSI-H, MSI-L, or MSS; etc.), confidence levels (e.g., associated with binary status determinations and/or classifications; etc.), identifiers (e.g., sample identifiers; sample labels indicating association with microsatellite stability or microsatellite instability; etc.), values along a spectrum, and/or any other suitable types of values. Any suitable types of data described herein can be used as inputs (e.g., for different models, such as background models, described herein; for portions of embodiments the method 100; etc.), generated as outputs (e.g., of models such as background models), and/or manipulated in any suitable manner for any suitable components associated with embodiments of the method 100 and/or system 200.

One or more instances and/or portions of embodiments of the method 100 and/or processes described herein can be performed asynchronously (e.g., sequentially), concurrently (e.g., in parallel; concurrently on different threads for parallel computing to improve system processing ability for microsatellite instability detection; etc.), in temporal relation to a trigger event (e.g., performance of a portion of the method 100), and/or in any other suitable order at any suitable time and frequency by and/or using one or more instances of embodiments of the system 200, components, and/or entities described herein.

Embodiments of the system 200 can include one or more: sample handling systems 210 (e.g., for processing samples; for sequencing library generation; etc.); sequencing systems 220 (e.g., for sequencing one or more sequencing libraries; etc.); computing systems 230 (e.g., for model generation, application; for microsatellite instability characterization determination; for any suitable computational processes; etc.); assays 240 (e.g., employing one or more portions of embodiments of the method 100, such as for microsatellite instability characterization; etc.); and/or any other suitable components.

Embodiments of the system 200 and/or portions of embodiments of the system 200 can entirely or partially be executed by, hosted on, communicate with, and/or otherwise include one or more: remote computing systems (e.g., a server, at least one networked computing system, stateless, stateful; etc.), local computing systems, user devices (e.g., mobile phone device, other mobile device, personal computing device, tablet, wearable, head-mounted wearable computing device, wrist-mounted wearable computing device, etc.), databases (e.g., including sample data and/or analyses, sequencing data, user data, data described herein, etc.), application programming interfaces (APIs) (e.g., for accessing data described herein, etc.) and/or any suitable components. Communication by and/or between any components of the system and/or other suitable components can include wireless communication (e.g., WiFi, Bluetooth, radiofrequency, Zigbee, Z-wave, etc.), wired communication, and/or any other suitable types of communication.

Components of embodiments of the system 200 can be physically and/or logically integrated in any manner (e.g., with any suitable distributions of functionality across the components, such as in relation to portions of embodiments of the method 100; etc.).

Portions of embodiments of the method 100 and/or system 200 are preferably performed by a first party but can additionally or alternatively be performed by one or more third parties, users, and/or any suitable entities.

However, embodiments of the method 100 and/or system 200 can be configured in any suitable manner.

2.1 Determining a Microsatellite-Related Background Model.

Embodiments of the method 100 can include determining a microsatellite-related background model Silo, which can function to account for sequencing-related errors (e.g., account for homopolymer-associated sequencing errors; accounting for artifacts of sequencing, alignment errors, rare variants unrelated to microsatellite instability; etc.) and/or facilitate loci determination (e.g., based on distance between a microsatellite stability background model and samples associated with microsatellite instability, such as in relation to variant allele frequency (VAF); etc.), microsatellite instability characterization (e.g., based on a sample's distance to a microsatellite stability background model and/or microsatellite instability background model, such as in relation to VAF, etc.), and/or other suitable processing (e.g., portions of embodiments of the method 100; etc.).

Microsatellite-related background models can include one or more of: microsatellite stability background models (e.g., generated from samples associated with microsatellite stability; etc.); microsatellite instability background models (e.g., generated from samples with microsatellite instability; MSI-L background models; MSI-H background models; etc.); allele-specific background models (e.g., based on VAF); and/or any other suitable type of background models. Microsatellite-related background models are preferably based on (e.g., generated based on; use; include; describe; indicate; etc.) VAF.

In examples, average observed VAFs based on sequence read alignments (e.g., outputs from sequencing systems; etc.) can be used in generating a microsatellite-related background model. In specific examples, average observed VAFs can be used in generating microsatellite stability background models (e.g., MSS background models, such as based on read alignments from samples associated with a plurality of cancer types and low MSI incidence rates, such as selected The Cancer Genome Atlas (TCGA) genomes; etc.), microsatellite instability background models (e.g., MSI-H background models; MSI-L background models; MSI background models; such as based on read alignments from samples associated with a plurality of cancer types and high MSI incidence rates; etc.), and/or any other suitable models.

Additionally or alternatively, microsatellite-related background models can be based on any suitable data types. In examples, all mono- and di-nucleotide repeat tracts from sequencing data for a set of samples (e.g., associated with MSS; associated with MSI; etc.) can be analyzed (e.g., in relation to VAF, etc.) for generation of one or more microsatellite-related background models; but any suitable samples and/or any suitable sequencing data can be used.

Figure 5:
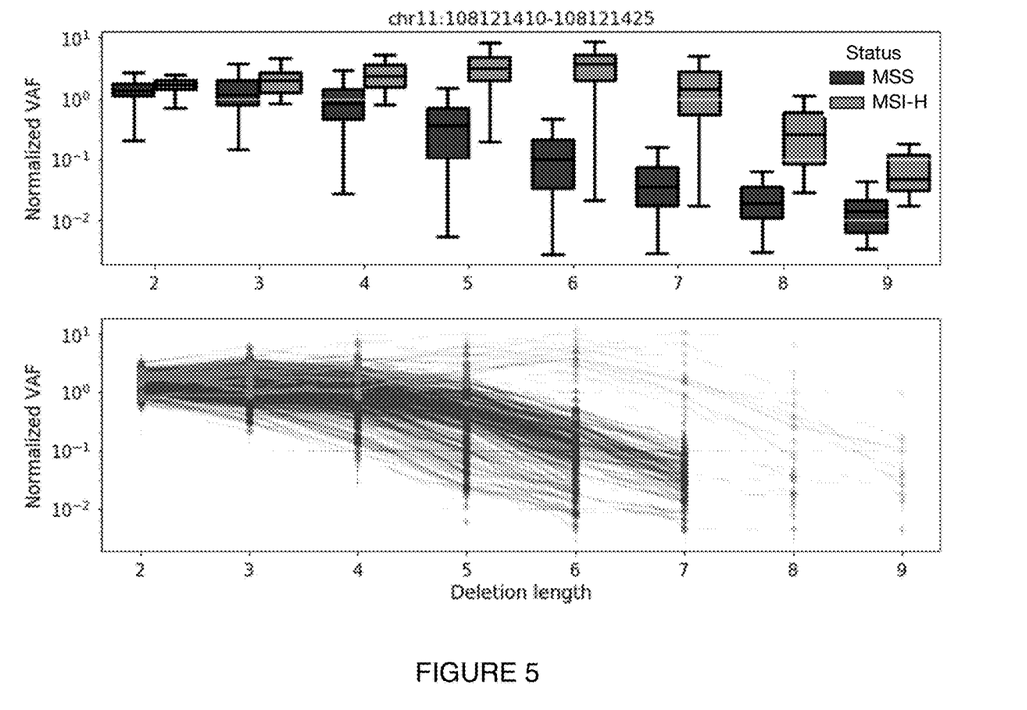
FIG. 5 includes a specific example of normalized variant allele frequencies for training samples in relation to deletion length.

In variations, determining a microsatellite-related background model can including performing one or more normalization processes (e.g., scale normalization processes; etc.), such as for mitigating sensitivity to variable homopolymer error-based indel scale (and/or other suitable sequencing-related errors; etc.). In specific examples, performing one or more normalization processes can enable normalization of observed data (e.g., observed VAF) while preserving biological signal. Normalization processes are preferably based on VAF (e.g., normalizing one or more allele-specific background models generated based on VAF, etc.), but can additionally or alternatively be based on any suitable data type. In an example, the microsatellite stability background model is determined based on a normalization of observed variant allele frequencies with a single-base deletion variant allele frequency. In an example, performing a scale normalization includes normalizing observed variant allele frequencies of the set of observed variant allele frequencies based on a single-base deletion variant allele frequency. In specific examples, VAF for single-base deletion at one or more loci (e.g., at each locus of a set of loci, etc.) can be used as a local control for normalizing VAFs of remaining deletions of various lengths (e.g., as shown in FIG. 5, which includes a specific example of normalized VAFs in relation to deletion length, for training samples associated with either MSS or MSI-H, etc.). In specific examples, scale normalization processes can enable testing for differences in the shape of the overall VAF profile of various length deletions at one or more loci (e.g., at each locus of a set of loci, etc.), such as for identifying loci associated with microsatellite instability, for determining one or more microsatellite instability characterizations, and/or for any suitable processes. However, performing one or more normalization processes can be performed in any suitable manner.

Additionally or alternatively, determining microsatellite-related background models, microsatellite-related background models themselves, other suitable models (e.g., microsatellite instability characterization models; etc.), suitable portions of embodiments of the method 100, and/or suitable portions of embodiments of the system 200, can include, apply, employ, perform, use, be based on, and/or otherwise be associated with one or more processing operations: extracting features (e.g., associated with MSI; etc.), performing pattern recognition on data, fusing data from multiple sources, combination of values (e.g., averaging values, etc.), compression, conversion (e.g., digital-to-analog conversion, analog-to-digital conversion), performing statistical estimation on data (e.g. ordinary least squares regression, non-negative least squares regression, principal components analysis, ridge regression, etc.), wave modulation, normalization, updating, ranking, weighting, validating, filtering (e.g., for baseline correction, data cropping, etc.), noise reduction, smoothing, filling, aligning, model fitting, binning, windowing, clipping, transformations, mathematical operations (e.g., derivatives, moving averages, summing, subtracting, multiplying, dividing, etc.), data association, multiplexing, demultiplexing, interpolating, extrapolating, clustering, image processing techniques, other signal processing operations, other image processing operations, visualizing, and/or any other suitable processing operations.

Additionally or alternatively, determining microsatellite-related background models, microsatellite-related background models themselves, other suitable models (e.g., microsatellite instability characterization models; etc.), suitable portions of embodiments of the method 100, suitable portions of embodiments of the system 200, can include, apply, employ, perform, use, be based on, and/or otherwise be associated with artificial intelligence approaches (e.g., machine learning approaches, etc.) including any one or more of: supervised learning (e.g., using logistic regression, using back propagation neural networks, using random forests, decision trees, etc.), unsupervised learning (e.g., using an Apriori algorithm, using K-means clustering), semi-supervised learning, a deep learning algorithm (e.g., neural networks, a restricted Boltzmann machine, a deep belief network method, a convolutional neural network method, a recurrent neural network method, stacked auto-encoder method, etc.), reinforcement learning (e.g., using a Q-learning algorithm, using temporal difference learning), a regression algorithm (e.g., ordinary least squares, logistic regression, stepwise regression, multivariate adaptive regression splines, locally estimated scatterplot smoothing, etc.), an instance-based method (e.g., k-nearest neighbor, learning vector quantization, self-organizing map, etc.), a regularization method (e.g., ridge regression, least absolute shrinkage and selection operator, elastic net, etc.), a decision tree learning method (e.g., classification and regression tree, iterative dichotomiser 3, C4.5, chi-squared automatic interaction detection, decision stump, random forest, multivariate adaptive regression splines, gradient boosting machines, etc.), a Bayesian method (e.g., naïve Bayes, averaged one-dependence estimators, Bayesian belief network, etc.), a kernel method (e.g., a support vector machine, a radial basis function, a linear discriminate analysis, etc.), a clustering method (e.g., k-means clustering, expectation maximization, etc.), an associated rule learning algorithm (e.g., an Apriori algorithm, an Eclat algorithm, etc.), an artificial neural network model (e.g., a Perceptron method, a back-propagation method, a Hopfield network method, a self-organizing map method, a learning vector quantization method, etc.), a dimensionality reduction method (e.g., principal component analysis, partial lest squares regression, Sammon mapping, multidimensional scaling, projection pursuit, etc.), an ensemble method (e.g., boosting, bootstrapped aggregation, AdaBoost, stacked generalization, gradient boosting machine method, random forest method, etc.), and/or any suitable artificial intelligence approach.

Microsatellite-related background models and/or any suitable models (e.g., microsatellite instability characterization models; etc.) can include any one or more of: probabilistic properties, heuristic properties, deterministic properties, and/or any other suitable properties.

Each model can be run or updated: once; at a predetermined frequency; every time a portion of an embodiment of the method 100 is performed; every time a trigger condition is satisfied (e.g., determining of new sequencing outputs for new samples; etc.), and/or at any other suitable time and frequency. Models can be run or updated concurrently with one or more other models, serially, at varying frequencies, and/or at any other suitable time. Each model can be validated, verified, reinforced, calibrated, or otherwise updated based on newly received, up-to-date data; historical data or be updated based on any other suitable data.

Different models (e.g., applying different algorithms; using different sets of features; associated with different input and/or output types; applied in different manners such as in relation to time, frequency, component applying the model; generated with different approaches; etc.) can be generated, selected, retrieved, executed, applied, and/or otherwise processed based on one or more of: locus (e.g., different models for different loci); data types (e.g., different models for VAF data type and for other data types; etc.); users (e.g., different models for users with different demographics, user characteristics, user preferences, etc.); microsatellite instability-associated conditions (e.g., different models for different cancer types; etc.); treatments (e.g., different models for different types of treatments; etc.); and/or any other suitable criteria. However, any suitable number and/or types of models can be applied in any suitable manner based on any suitable criteria.

VAFs, read alignments, sequencing outputs, and/or suitable sequencing-related data can be determined based on sequencing (e.g., samples associated with microsatellite stability or microsatellite instability; etc.) using any suitable sequencing technologies (e.g., next-generation sequencing systems, semiconductor-based sequencing systems such as Thermo Fisher Scientific Ion Torrent sequencing systems; etc.). In a specific example, determining the microsatellite stability background model includes determining the microsatellite stability background model based on the set of observed variant allele frequencies determined from sequencing nucleic acid material from the first set of samples using a next-generation sequencing system associated with homopolymer-associated errors. However, determining microsatellite stability background models can be associated with (e.g., based on, apply, include, etc.) any suitable sequencing technologies.

However, determining microsatellite-related background models Silo can be performed in any suitable manner.

2.2 Determining a Locus.

Embodiments of the method 100 can include determining one or more loci (e.g., a set of loci) associated with microsatellite instability S120, which can function to identify one or more loci (e.g., sequence positions; etc.) associated with (e.g., indicative of; as a target of analysis; etc.) microsatellite instability (e.g., identifying loci most enriched for length polymorphisms, such as with VAFs in excess of background relative to a reference population; etc.), such as for facilitating microsatellite instability characterization, treatment provision, and/or suitable portions of the method 100.

Determining one or more loci associated with MSI is preferably based on one or more microsatellite-related background models. In examples, samples associated with MSI can be compared (e.g., in relation to VAF, in relation to any suitable MSI-related metric; etc.) to a microsatellite stability background model (e.g., generated from samples associated with low MSI incidence; etc.), to identify loci with greatest distance between the samples associated with MSI and the microsatellite stability background model. In a specific example, the set of loci can be determined based on the microsatellite stability background model and a set of samples associated with the microsatellite instability. In examples, first samples associated with MSS can be compared (e.g., in relation to VAF, in relation to any suitable MSI-related metric; etc.) to second samples associated with MSI, to identify the loci with greatest separation (e.g., distance) between the first and second samples. In a specific example, determining the set of loci can include: determining a set of distances (e.g., Mahalanobis distances corresponding to the Mahalanobis distance type; etc.) based on the microsatellite stability background model and the set of samples associated with the microsatellite instability; and determining the set of loci based on the set of distances (e.g., Mahalanobis distances, etc.).

Determining one or more loci associated with MSI can include ranking a set of loci (e.g., and/or selecting a set number of loci from the highest-ranking loci), such as based on, for each locus, distance between (e.g., in relation to VAF and/or other suitable metrics, etc.) samples associated with MSI and one or more microsatellite stability background models.

Determining one or more loci can be based on Mahalanobis distances corresponding to a Mahalanobis distance type. In a specific example, each locus can be ranked according to an average Mahalanobis distance between each training sample associated with MSI and a microsatellite stability background model. In a specific example, a set of loci can be determined based on a set of Mahalanobis distances derived from the microsatellite background model and the set of samples associated with the microsatellite instability.

Mahalanobis distance (e.g., in relation to determining loci; in relation to determining one or more microsatellite instability characterizations; in relation to any suitable portions of embodiments of the method 100; etc.) can characterize the distance between a point and a distribution, can account for correlation between variables, can be used in classification problems, and/or can possess other suitable characteristics for use in portions of embodiments of the method 100 (e.g., determining one or more loci; determining one or more microsatellite instability characterizations; etc.). Mahalanobis distance can be in the form of:

$$D_M(\vec{x}) = \sqrt{(\vec{x} - \vec{\mu})^T S^{-1}(\vec{x} - \vec{\mu})}$$

where $D_M$ is the Mahalanobis distance, of an observation $\vec{x} = (x_1, x_2, x_3, \ldots, x_N)^T$ from a set of observations with mean $\vec{\mu} = (\mu_1, \mu_2, \mu_3, \ldots, \mu_N)^T$, where S is the covariance matrix.

Additionally or alternatively, determining one or more loci can be based on one or more of: sequencing read depth such as average read depth (e.g., average sequencing read depth and/or suitable read depth parameters associated with sequencing of any suitable samples, such as samples used for a microsatellite-related background model used in determining loci, such as samples associated with MSI, etc.), tract length (e.g., DNA tract length associated with any suitable loci, samples, etc.), typical strand bias (e.g., typical biases and/or degree of error associated with sequencing technologies and/or suitable aspects associated with DNA and/or sequencing; etc.), and/or any suitable data. In an example, the set of loci can be determined based on the microsatellite stability background model, the set of samples associated with the microsatellite instability, and at least one of average read depth, tract length, and typical strand bias.

In specific examples, samples (e.g., VAF associated with the samples, etc.) used for determining one or more loci can be associated with one or more cancer types, other suitable microsatellite instability-associated conditions, microsatellite stability, microsatellite instability, and/or any suitable characteristics.

Any suitable number of loci (e.g., one or more loci) can be determined (e.g., 8 loci, any suitable number; etc.), using similar processes (e.g., similar processing operations; similar inputs; similar algorithms; etc.), different processes (e.g., based on any suitable criteria; etc.), and/or any suitable processes.

However, determining one or more loci S120 can be performed in any suitable manner.

2.3 Determining a Microsatellite Instability Characterization.

Embodiments of the method 100 can include determining one or more microsatellite instability characterizations S130, which can function to determine characterizations of microsatellite stability or microsatellite instability for one or more users (e.g., for use in treatment response evaluation; for use in diagnostics; for use in facilitating treatment provision; etc.).

Microsatellite instability characterizations preferably include a determination of microsatellite stability or microsatellite instability (e.g., MSI; MSI-L; MSI-H; etc.) for a sample and/or user. For example, a microsatellite instability characterization can include a binary status determination between microsatellite instability such as MSI-H, and microsatellite stability such as MSS. Microsatellite instability characterizations are preferably associated with (e.g., indicative of, correlated with, describing a characteristics regarding, informative of, etc.) at least one cancer condition (e.g., at least one cancer type), but can additionally or alternatively be associated with any suitable microsatellite instability-associated condition. Additionally or alternatively microsatellite instability characterizations can include any one or more of: classifications (e.g., between different types of microsatellite stability and/or microsatellite instability, such as MSS, MSI-L, MSI-H; etc.), risk characterizations (e.g., risk scores for developing and/or the presence of microsatellite instability-associated conditions; risk of microsatellite instability; etc.); diagnoses (e.g., presence or absence of one or more microsatellite instability-associated conditions; etc.); information regarding microsatellite instability and/or microsatellite instability-associated conditions (e.g., regarding symptoms, signs, triggers, associated conditions, etc.); diagnostic recommendations (e.g., to seek care providers for performing additional diagnostic processes; etc.); reports; comparisons (e.g., comparisons with other subgroups, populations, users; such as comparison of VAF or other suitable metrics between a user and a population associated with microsatellite stability, between a user and a population associated with microsatellite instability; etc.); treatment determinations; other suitable outputs associated with microsatellite instability characterization; and/or any other suitable data.

Determining a microsatellite instability characterization preferably includes determining one or more microsatellite instability parameters. Microsatellite instability parameters can include one or more of: distances (e.g., distances between models and samples, such as VAFs and/or other suitable parameters associated with samples; distance between samples, such as between a user sample and one or more sets of samples associated with microsatellite stability and/or microsatellite instability; etc.); VAF parameters (e.g., average observed VAF, VAF for different length deletions, parameters associated with VAF, etc.); aggregate microsatellite instability parameters (e.g., combinations of individual microsatellite instability parameters, such as log likelihood ratios of individual microsatellite instability parameters, etc.); and/or any other suitable parameters. In examples, microsatellite instability parameters can include Mahalanobis distances (e.g., corresponding to Mahalanobis distance type) and/or parameters determined based on Mahalanobis distance (e.g., log-likelihood ratios of Mahalanobis distances), such as where Mahalanobis distances can be used in determining distances between user samples and different microsatellite-related background models (e.g., a distance between a user sample and a MSS background model; a distance between a user sample and a MSI background model; such as in relation to VAFs and/or other suitable metrics; etc.), such as while handling in-sample correlation between normalized VAFs for deletions of different lengths. Additionally or alternatively, microsatellite instability parameters can include any suitable distances (e.g., Bregman divergence types; Bhattacharyya distances; Hellinger distances; Hamming distances; other suitable similarity or difference metrics; etc.) and/or parameter types.

Determining one or more microsatellite instability characterizations is preferably based on one or more microsatellite instability parameters (e.g., where microsatellite instability parameters can be based on microsatellite-related background models, loci, etc.), microsatellite-related background models, one or more loci associated with microsatellite instability, and/or any suitable aspects. In a specific example, determining a microsatellite instability parameter (e.g., a log-likelihood ratio of distances) can include determining a first distance based on the microsatellite stability background model and the user sample (e.g., a distance, in relation to VAF, between the microsatellite stability background model and the user sample, etc.); determining a second distance based on a microsatellite instability background model and the user sample (e.g., a distance, in relation to VAF, between the microsatellite instability background model and the user sample, etc.); and determining the microsatellite instability parameter based on the first and the second distances. In a specific example, determining the microsatellite instability parameter can include: determining a set of microsatellite stability distances including the first distance, based on the microsatellite stability background model and the user sample (e.g., distances, such as in relation to VAF, between the user sample and the microsatellite stability background model, such as where the microsatellite stability background model is generated from samples associated microsatellite stability; etc.), where each microsatellite stability distance of the set of microsatellite stability distances corresponds to a different locus of the set of loci associated with microsatellite instability; determining a set of microsatellite instability distances including the second distance, based on the microsatellite instability background model and the user sample (e.g., distances, such as in relation to VAF, between the user sample and the microsatellite instability background model, such as where the microsatellite instability background model is generated from samples associated microsatellite instability; etc.), where each microsatellite instability distance of the set of microsatellite instability distances corresponds to a different locus of the set of loci; and determining the microsatellite instability parameter based on the set of microsatellite stability distances and the set of microsatellite instability distances. In a specific example, set of microsatellite stability distances and the set of microsatellite instability distances correspond to a Mahalanobis distance type (e.g., the microsatellite stability distances and the microsatellite instability distance include Mahalanobis distances; etc.).

In a specific example, determining the microsatellite instability parameter can include determining a per-locus log-likelihood ratio for each locus of the set of loci (e.g., associated with microsatellite instability; loci determined as in S120; etc.) based on the set of microsatellite stability distances and the set of microsatellite instability distances corresponding to the Mahalanobis distance type; and determining the microsatellite instability parameter based on the per-locus log-likelihood ratios (e.g., averaging the per-locus log-likelihood ratios to determine a scalar value, such as for comparing to a microsatellite instability threshold; etc.). In a specific example, determining a microsatellite instability characterization can include determining a standard log-likelihood ratio of Mahalanobis distances between (e.g., in relation to VAFs; in relation to any suitable metrics; etc.) a user sample (e.g., a sample under test; etc.) and both microsatellite stability model(s) and microsatellite instability model(s) (and/or any suitable type and/or number of microsatellite-related models; etc.), such as in relation to each locus of a set of loci (e.g., determined as in S120), where each individual log-likelihood ratio of Mahalanobis distances (and/or other suitable distance types) for each locus can be combined (e.g., averaged) into a scalar value (e.g., for comparison to a microsatellite instability threshold; etc.).

In specific examples, the microsatellite instability parameter can include a log-likelihood ratio of distances, and/or an overall log-likelihood ratio of distances (e.g., by averaging per-locus log-likelihood ratio of distances), such as a log-likelihood ratio of Mahalanobis distances, such as where the log-likelihood ratio of distances can be in the form of:

$$l = \log_{10}\left(\frac{D_{MSS}}{D_{MSI}}\right)$$

where $D_{MSS}$ is the distance to one or more microsatellite stability background models (e.g., distance between a user sample and the microsatellite stability background model, such as in relation to VAFs and/or other suitable metrics, such as VAFs for a set of loci associated with microsatellite instability; etc.) and/or other suitable model associated with microsatellite stability; and where $D_{MSI}$ is the distance to one or more microsatellite instability background model (e.g., distance between a user sample and the microsatellite instability background model, such as in relation to VAFs and/or other suitable metrics, such as VAFs for a set of loci associated with microsatellite instability; etc.) and/or other suitable model associated with microsatellite instability; where l is the log-likelihood ratio (e.g., where values of 0 indicate equal likelihood between MSI and MSS; where positive values indicate a greater likeliness of MSI; where negative values indicate a greater likeliness of MSS; such as where l=1 when $D_{MSS}$=10 and $D_{MSI}$=1; etc.).

In a specific example, determining a microsatellite instability parameter for a user associated with a user sample can be based on the user sample and a set of loci associated with microsatellite instability, where determining the microsatellite instability parameter includes: determining a microsatellite stability distance for the user based on the user sample and a microsatellite stability background model associated with first variant allele frequencies from first samples associated with microsatellite stability, and determining a microsatellite instability distance for the user based on the user sample and a microsatellite instability background model associated with second variant allele frequencies from second samples associated with the microsatellite instability; and determining a microsatellite instability characterization for the user based on the microsatellite instability parameter.

Additionally or alternatively, determining microsatellite instability parameters associated with a one or more loci can be performed in any suitable manner. However, determining microsatellite instability parameters and/or microsatellite instability characterizations can be performed in any suitable manner.

Determining a microsatellite instability characterization can be based on one or more microsatellite instability thresholds (and/or microsatellite instability parameters and/or other suitable data; etc.), such as where determining microsatellite instability characterizations can additionally or alternatively include determining one or more microsatellite instability thresholds; comparing one or more microsatellite instability thresholds to one or more microsatellite instability parameters (e.g., determined for a user; etc.); and/or any suitable processes associated with thresholds.

Determining one or more microsatellite instability thresholds can be based on a set of loci associated with microsatellite instability, and a set of samples associated with microsatellite stability and microsatellite instability (e.g., where the set of samples includes a first subset of samples associated with microsatellite stability, and a second subset of samples associated with microsatellite instability; etc.). In a specific example, the microsatellite instability threshold can include an overall log-likelihood ratio of distances (e.g., Mahalanobis distances; such as an overall l log-likelihood ratio of distances; etc.), such as based on combining (e.g., averaging) individual per-locus log-likelihood ratios of distances (e.g., Mahalanobis distances; individual l log-likelihood ratios of distances; etc.) for the set of samples. In a specific example, determining microsatellite instability threshold can be based on balancing sensitivity and specificity performance on training samples with overall prevalence rates across a set of samples associated with a plurality of cancer types (and/or other suitable microsatellite instability-associated conditions; etc.), microsatellite stability, microsatellite instability, and/or any other suitable characteristics. In a specific example, overall log-likelihood ratio of distances for a user can be compared to a microsatellite instability threshold (e.g., an overall log-likelihood ratio of distances threshold, etc.) for determination of one or more microsatellite instability characterizations. In a specific example, determining the microsatellite instability characterization for the user includes determining a binary status determination for the microsatellite instability based on the comparison between the microsatellite instability parameter and the microsatellite instability threshold. In a specific example, determining the microsatellite instability characterization includes classifying the user with the microsatellite instability based on the microsatellite instability parameter and a microsatellite instability threshold associated with the set of loci. However, using microsatellite instability thresholds can be performed in any suitable manner.

Determining one or more microsatellite instability characterizations can include generating (e.g., training, etc.), applying, executing, updating, and/or otherwise processing one or more microsatellite instability characterization models, such as based on and/or using any suitable processing operations, artificial intelligence approaches, and/or suitable approaches described herein.

Microsatellite instability characterizations, microsatellite instability parameters, and/or other suitable data can be determined based on sequencing (e.g., of user samples, etc.) using any suitable sequencing technologies (e.g., next-generation sequencing systems, semiconductor-based sequencing systems such as Thermo Fisher Scientific Ion Torrent sequencing systems; etc.). In a specific example, determining a microsatellite instability parameter can include determining a microsatellite instability parameter based on sequencing of the user sample using a semiconductor-based sequencing system (e.g., associated with homopolymer-associated errors; etc.) (and/or on the set of loci and/or any other suitable aspects).

However, determining one or more microsatellite instability characterizations S130 can be performed in any suitable manner.

2.4 Facilitating Treatment Provision.

Embodiments of the method 100 can additionally or alternatively include facilitating treatment provision for one or more users, which can function to cause, present, provide, administer, aid, and/or otherwise facilitate treatment provision for one or more users in relation to one or more microsatellite instability-associated conditions.

Facilitating treatment provision can include any one or more of: transmitting and/or presenting microsatellite instability characterizations (e.g., to any suitable entities, such as clinical trial administrators, care providers, etc.); guiding medical decision-making, such as is in relation to experiment administration (e.g., clinical trial administration), healthcare, and/or other suitable processes; determining one or more treatments (e.g., using a treatment model; etc.) for one or more microsatellite instability-associated conditions; providing recommendations regarding treatments, treatment responses, and/or other suitable aspects; and/or other suitable processes associated with treatment provision. Treatments can include any one or more of: cancer treatments (e.g., pembrolizumab, durvalumab, avelumab, atezolizumab, nivolumab; other immunotherapy agents; any suitable immune therapy treatments; etc.); consumables; drugs; surgical procedures; any suitable treatments associated with one or more microsatellite instability-associated conditions; and/or any suitable treatments.

Facilitating treatment provision is preferably based on one or more microsatellite instability characterizations. In an example, the method 100 can include facilitating treatment provision for the user for at least one cancer condition based on the microsatellite instability characterization. In an example, the method 100 causing treatment provision for the user for at least one cancer condition based on the microsatellite instability characterization. In a specific example, microsatellite instability characterizations indication a status determination of MSI can be used in selecting users for clinical trials, selecting users as amenable to treatments (e.g., positive response to pembrolizumab, etc.), and/or be used in any suitable manner (e.g., used in processes associated with determination of MSI, etc.). Additionally or alternatively, facilitating treatment provision can be based on any suitable data (e.g., based on presence of additional biomarkers; etc.). In examples, microsatellite instability characterizations and other suitable characterizations (e.g., indicating treatment response, diagnoses, etc.) can be used in combination to facilitate treatment provision, to detect one or more conditions, and/or perform any suitable processes (e.g., portions of embodiments of the method 100, etc.).

However, facilitating treatment provision S140 can be performed in any suitable manner.

3. Other.

Embodiments of the method 100 and/or system 200 can include every combination and permutation of the various system components and the various method processes, including any variants (e.g., embodiments, variations, examples, specific examples, figures, etc.), where portions of embodiments of the method 100 and/or processes described herein can be performed asynchronously (e.g., sequentially), concurrently (e.g., in parallel), or in any other suitable order by and/or using one or more instances, elements, components of, and/or other aspects of the system 200 and/or other entities described herein.

Any of the variants described herein (e.g., embodiments, variations, examples, specific examples, figures, etc.) and/or any portion of the variants described herein can be additionally or alternatively combined, aggregated, excluded, used, performed serially, performed in parallel, and/or otherwise applied.

Portions of embodiments of the method 100 and/or system 200 can be embodied and/or implemented at least in part as a machine configured to receive a computer-readable medium storing computer-readable instructions. The instructions can be executed by computer-executable components that can be integrated with embodiments of the system 200. The computer-readable medium can be stored on any suitable computer-readable media such as RAMs, ROMs, flash memory, EEPROMs, optical devices (CD or DVD), hard drives, floppy drives, or any suitable device. The computer-executable component can be a general or application specific processor, but any suitable dedicated hardware or hardware/firmware combination device can alternatively or additionally execute the instructions.

As a person skilled in the art will recognize from the previous detailed description and from the figures and claims, modifications and changes can be made to embodiments of the method 100, system 200, and/or variants without departing from the scope defined in the claims. Variants described herein not meant to be restrictive. Certain features included in the drawings may be exaggerated in size, and other features may be omitted for clarity and should not be restrictive. The figures are not necessarily to scale. Section titles herein are used for organizational convenience and are not meant to be restrictive. The description of any variant is not necessarily limited to any section of this specification.

We claim:

1. A method comprising:
   determining a microsatellite stability background model based on a set of observed variant allele frequencies from a first set of samples associated with microsatellite stability, wherein determining the microsatellite stability background model comprises performing a scale normalization based on the observed variant allele frequencies;
   determining a set of loci associated with microsatellite instability based on the microsatellite stability background model and a second set of samples associated with the microsatellite instability;
   determining a microsatellite instability threshold based on the set of loci and a third set of samples associated with the microsatellite stability and the microsatellite instability;
   determining a microsatellite instability parameter for a user associated with a user sample, based on the user sample and the set of loci;
   determining a microsatellite instability characterization of high (MSI-H), associated with the at least one cancer condition, for the user based on a comparison between the microsatellite instability parameter and the microsatellite instability threshold; and
   administering at least one of pembrolizumab, durvalumab, avelumab, atezolizumab, or nivolumab to the user having a determined microsatellite instability characterization of MSI-H.

2. The method of claim 1, wherein determining the microsatellite instability parameter comprises:
   determining a first distance based on the microsatellite stability background model and the user sample;

determining a second distance based on a microsatellite instability background model and the user sample; and determining the microsatellite instability parameter based on the first and the second distances.

3. The method of claim 2, wherein determining the microsatellite instability parameter comprises:

determining a set of microsatellite stability distances comprising the first distance, based on the microsatellite stability background model and the user sample, wherein each microsatellite stability distance of the set of microsatellite stability distances corresponds to a different locus of the set of loci;

determining a set of microsatellite instability distances comprising the second distance, based on the microsatellite instability background model and the user sample, wherein each microsatellite instability distance of the set of microsatellite instability distances corresponds to a different locus of the set of loci; and determining the microsatellite instability parameter based on the set of microsatellite stability distances and the set of microsatellite instability distances.

4. The method of claim 3, wherein the third set of samples is associated with a plurality of cancer types comprising the at least one cancer condition.

5. The method of claim 3, wherein the set of microsatellite stability distances and the set of microsatellite instability distances correspond to a Mahalanobis distance type.

6. The method of claim 5, wherein determining the microsatellite instability parameter comprises:

determining a per-locus log-likelihood ratio for each locus of the set of loci based on the set of microsatellite stability distances and the set of microsatellite instability distances corresponding to the Mahalanobis distance type; and determining the microsatellite instability parameter based on the per-locus log-likelihood ratios.

7. The method of claim 5, wherein determining the set of loci comprises:

determining a set of Mahalanobis distances corresponding to the Mahalanobis distance type, based on the microsatellite stability background model and the second set of samples associated with the microsatellite instability; and determining the set of loci based on the set of Mahalanobis distances.

8. The method of claim 2, wherein determining the microsatellite instability characterization for the user as MSI-H comprises determining a binary status determination for the microsatellite instability based on the comparison between the microsatellite instability parameter and the microsatellite instability threshold.

9. The method of claim 1, wherein performing the scale normalization comprises normalizing observed variant allele frequencies of the set of observed variant allele frequencies based on a single-base deletion variant allele frequency.

10. The method of claim 1, wherein determining the microsatellite stability background model comprises determining the microsatellite stability background model based on the set of observed variant allele frequencies determined from sequencing nucleic acid material from the first set of samples using a next-generation sequencing system associated with homopolymer-associated errors.

11. A method comprising:

determining a microsatellite instability parameter for a user associated with a user sample, based on the user sample and a set of loci associated with microsatellite instability, wherein determining the microsatellite instability parameter comprises:

determining a microsatellite stability distance for the user based on the user sample and a microsatellite stability background model associated with first variant allele frequencies from first samples associated with microsatellite stability, and determining a microsatellite instability distance for the user based on the user sample and a microsatellite instability background model associated with second variant allele frequencies from second samples associated with the microsatellite instability;

determining a microsatellite instability characterization of high (MSI-H) for the user based on the microsatellite instability parameter; and administering at least one of pembrolizumab, durvalumab, avelumab, atezolizumab, or nivolumab to the user having a determined microsatellite instability characterization of MSI-H.

12. The method of claim 11, wherein the set of loci is determined based on the microsatellite stability background model and a set of samples associated with the microsatellite instability.

13. The method of claim 12, wherein the set of loci is determined based on a set of Mahalanobis distances derived from the microsatellite background model and the set of samples associated with the microsatellite instability.

14. The method of claim 12, wherein the set of loci is determined based on the microsatellite stability background model, the set of samples associated with the microsatellite instability, and at least one of average read depth, tract length, and typical strand bias.

15. The method of claim 12, wherein the set of samples is associated with a plurality of cancer types.

16. The method of claim 1, wherein the microsatellite stability background model is determined based on a normalization of observed variant allele frequencies with a single-base deletion variant allele frequency.

17. The method of claim 11, wherein determining the microsatellite instability characterization as MSI-H comprises classifying the user with the microsatellite instability based on the microsatellite instability parameter and a microsatellite instability threshold associated with the set of loci.

18. The method of claim 11, wherein determining the microsatellite instability parameter as MSI-H comprises determining the microsatellite instability parameter based on the set of loci and sequencing of the user sample using a semiconductor-based sequencing system associated with homopolymer-associated errors.

* * * * *